United States Patent
Susilo

(10) Patent No.: US 7,101,901 B2
(45) Date of Patent: Sep. 5, 2006

(54) 2-METHYLTHIAZOLIDINE-2,4-DICARBOXYLIC ACID AND SALTS THEREOF FOR THE TREATMENT OF NEURODEGENERATIVE DISEASES

(76) Inventor: Rudy Susilo, Peterstrasse 14a, 50999 Köln (DE)

( * ) Notice: Subject to any disclaimer, the term of this patent is extended or adjusted under 35 U.S.C. 154(b) by 114 days.

(21) Appl. No.: 10/504,069

(22) PCT Filed: Feb. 24, 2003

(86) PCT No.: PCT/DE03/00573

§ 371 (c)(1),
(2), (4) Date: Aug. 5, 2004

(87) PCT Pub. No.: WO03/072101

PCT Pub. Date: Sep. 4, 2003

(65) Prior Publication Data

US 2005/0148641 A1    Jul. 7, 2005

(30) Foreign Application Priority Data

Feb. 22, 2002  (EP) .................................. 02003983

(51) Int. Cl.
*A61K 31/427* (2006.01)
*C07D 277/06* (2006.01)

(52) U.S. Cl. ...................................... 514/365; 548/201

(58) Field of Classification Search ................ 548/201; 514/365

See application file for complete search history.

(56) References Cited

U.S. PATENT DOCUMENTS 3,730,724 A * 5/1973 Abbott ....................... 430/505
6,441,011 B1 * 8/2002 Susilo et al. ................ 514/369

FOREIGN PATENT DOCUMENTS

DE        2116629        10/1972
DE        19857690 A1 *  6/2000

OTHER PUBLICATIONS

International Search Report, PCT/DE03/00573, Jul. 21, 2003.

* cited by examiner

*Primary Examiner*—Joseph K. McKane
*Assistant Examiner*—Michael Barker
(74) *Attorney, Agent, or Firm*—Amin & Turocy, LLP

(57) ABSTRACT

The invention relates to the compounds (2R,4R), (2S,4R)-2-methylthiazolidine-2,4-dicarboxylic acid and (2RS,4R)-2-methylthiazolidine-2,4-dicarboxylic acid and salts of said compounds, the use thereof for the prophylaxis and/or treatment of neurodegenerative diseases, methods for the prophylaxis and/or treatment of neurodegenerative diseases, and pharmaceutical compositions containing said compounds together with physiologically compatible carriers, auxiliary agents, and/or solvents.

2 Claims, No Drawings

2-METHYLTHIAZOLIDINE-2,4-DICARBOXYLIC ACID AND SALTS THEREOF FOR THE TREATMENT OF NEURODEGENERATIVE DISEASES

The invention relates to the compounds (2R,4R)-, (2S,4R)-2-methylthiazolidine-2,4-dicarboxylic acid as well as (2RS,4R)-2-methylthiazolidine-2,4-dicarboxylic acid and salts of these compounds, their use for prophylaxis and/or treatment of neurodegenerative diseases, methods for prophylaxis and/or treatment of neurodegenerative diseases and pharmaceutic formulations, which comprise said compounds and/or salts thereof optionally together with further additives.

Cerebral circulatory disorders, ischemia, cerebral ischemia, apoplexy, cerebral apoplexy, brain deficiencies, senile dementia, Alzheimer's disease, Huntington's chorea and Parkinson's disease for example are counted among the neurodegenerative diseases.

The Parkinson's disease belongs to the frequent neurodegenerative diseases of senior persons.

The Parkinson's disease (or idiopathic Parkinson's syndrome) is a progressive disease, which is characterized by the symptoms of resting tremor, hypo-/bradykinesia and rigidity of the musculature. Neuropathologically viewed, a degeneration of the dopaminergic neurons, which project to the striatum, occurs in the substantia nigra with decrease of the striatal dopamine concentration as well as hyaline inclusion bodies (Lewy bodies) in the remaining neurons. Etiology and pathophysiology of this disease are widely unknown. The idiopathic Parkinson's syndrome accounts to the frequent neurological diseases of senior persons. The first symptoms occur usually after the age of 50 years, young persons are affected very seldom. The prevalence increases exponentially after the age of 60 years, such that about 1 to 1.5% of the persons above the age of 60 years are affected.

Via a symptomatic treatment by substitution of the dopamine deficiency, a treatment of the symptoms is possible for a period of 5 to 10 years. But at present the progression of the disease, i.e. the degeneration velocity of the dopaminergic neurons, cannot be influenced. The initially positive reports about a neuroprotective effect of the irreversible monoamine oxidase B-inhibitor selegiline did not approve in the long-term devolution.

Today, 3 categories of pharmaceuticals are available for the medicamentous Parkinson therapy.

Dopaminergics
L-DOPA plus decarboxylase inhibitor (e.g. Madopar®, Nacom®)
Dopamine agonists: bromocriptine (Pravidel®), lisuride (Dopergin®), pergolide (Parkotil®), dihydrocryptine (Almirid®), cabergoline, pramipexole, ropinirole
Monoamine oxidase B-inhibitors: selegiline (e.g. Deprenyl®)

Anticholinergics
Benzatropine (Cogentinol®), trihexyphenidyl (e.g. Artane®), biperiden (e.g. Akineton®)

Glutamate/NMDA receptor antagonists
Amantadine (e.g. PK-Merz®), memantine.

The precursor substance of the dopamine, the L-DOPA, is to be mentioned as first known dopaminergic. Contrary to dopamine, it can pass the hemato-encephalic barrier, then gets incorporated by the dopaminergic nerve cell and converted to dopamine by the cytosolic decarboxylase. L-DOPA is always combined with a decarboxylase inhibitor, that does not penetrate into the brain, such as benserazide (in Madopar®) or carbidopa (e.g. Nacom®) to inhibit a peripheral conversion to dopamine. In this combination L-DOPA is still considered as the most effective and the most compatible dopamimetic substance.

The dopamine agonists, which directly influence the striatal dopamine receptors, are another class of dopaminergics. The efficiency of all agonists is weaker than of L-DOPA, however, with these substances, complications such as cardiovascular complications as well as amentia and hallucinations appear more frequently, besides the known side effects of L-DOPA. For this reason, these substances have to be applied with caution to senior, multimorbid patients.

Selegiline (e.g. Movergan®, Deprenyl®) inhibits irreversibly the dopamine degrading monoamine oxidase B and leads to an increase of the dopamine concentration in the striatum. Its effect is weak. In the first year of treatment a neuroprotective effect could be shown which was however not detectable during the long-term treatment any more.

Anticholinergics reduce the resting tremor and the rigor, the hypokinesia is not influenced significantly. Due to their spectra of side effects (amentia up to psychosis, glaucoma, anuresis, vertigo, fatigue) anticholinergics should be applied only in case of severe indication to patients above the age of 65 years, to patients with cognitive deficiencies not at all.

The amantadines (e.g. PK-Merz®) and the mere weakly efficient memantine are available as glutamate/NMDA receptor antagonists. The effects of these two substance groups are weak in comparison to the above described dopaminergics.

Motoric late complications appear in many patients after long lasting application of dopaminergics as already mentioned above. A stabilisation of the blood level of L-DOPA (e.g. by application of retard preparations) is reasonable for treatment of these side effects. Further on, the reduction of the L-DOPA dose rate and higher dosage of a dopamine agonist preferably with long half-life (e.g. pergolide) is reasonable. A monotherapy can be attempted casually with an agonist (also in combination with amantadine). During stressing long-term off phases with painful dystonias the subcutaneous application of the dopamine agonist apomorphine cannot be abandoned in case of some patients. Many times the treatment of these late complications is overall unsatisfactory and requires an intensive cooperation of patient and physician. A stereotactic surgery can be considered as last option.

During dopaminergic medication the occurrence of psychoses is an additional complication. The incidence and gravity of this complication is determined by the age and possibly by other lesions of the brain, e.g. a vascular encephalopathy, in addition to the daily dose rate of the dopaminergic. Initially these medicament induced psychoses express themselves by unusually active dreams, illusionary cognitions and afterwards by visual, rarely also acoustical hallucinations and delusions (Dr. med. A. Storch, Dr. med. J. Schwarz, "Geriatrie Praxis", MMV Medizin Verlag GmbH München, Jahrgang 9 (1997) 4, 24–28).

Also surgical therapies of Parkinson's disease (transplantation of dopamine synthesizing cells into the striatum; intrathecal application of neurotrophic factors; structural or functional lesion of overactive core areas of the basal ganglions) are pursued in addition, which however do not represent an alternative to the medicamentous treatment, because of partially serious side effects.

The object of the present invention is to provide physiologically well compatible substances, which can be applied for prophylaxis and/or therapy of neurodegenerative diseases and furthermore avoid or at least reduce the side effects of the known medicaments.

This object is solved by the technical teaching of the independent claim 1 as well as the subject matters of the claims 5, 6, 9, and 11 of the present invention. Other favorable embodiments, aspects and details of the invention are evident from the dependent claims, the description and the examples.

Surprisingly it was found, that (2R,4R)-2-methylthiazolidine-2,4-dicarboxylic acid, (2S,4R)-2-methylthiazolidine-2,4-dicarboxylic acid as well as (2RS,4R)-2-methylthiazolidine-2,4-dicarboxylic acid and also the salts of these compounds can be used according to the invention for prophylaxis and/or therapy of neurodegenerative diseases. Parkinson's disease, Huntington's chorea, cerebral circulatory disorders, ischemia, cerebral ischemia, apoplexy, cerebral apoplexy, brain deficiencies, senile dementia or Alzheimer's disease shall be mentioned as examples of neurodegenerative diseases.

The salts of the above mentioned compound can be prepared by addition of basic solutions. Suitable bases are, for instance, alkaline and alkaline earth hydroxides, carbonates, hydrogen carbonates, phosphates or amines.

Salts of (2R,4R)-2-methylthiazolidine-2,4-dicarboxylic acid, (2S,4R)-2-methylthiazolidine-2,4-dicarboxylic acid and/or (2RS,4R)-2-methylthiazolidine-2,4-dicarboxylic acid with amino acids are especially suitable.

Alanine, asparagine, cysteine, glutamine, phenylalanine, glycine, histidine, isoleucine, lysine, leucine, methionine, arginine, serine, ornithine, threonine, valine, tryptophan, tyrosine or derivatives of these amino acids can be used as amino acids. Basic amino acids such as lysine, arginine or histidine are preferred. Moreover basic salts of amino acids such as sodium, potassium or lithium salts of amino acids or disodium, dipotassium or dilithium salts of glutaminic acid or arparaginic acid are preferred.

In addition to amino acids, salts can be formed also with alkaline and alkaline earth cations or transition metal ions. $Li^+$, $Na^+$, $K^+$, $Rb^+$, $Cs^+$, $Be^{2+}$, $Mg^{2+}$, $Ca^{2+}$, $Sc^{3+}$, $Mn^{2+}$, $Fe^{3+}$, $Cu^+$, $Cu^{2+}$, $Ag^+$ and $Zn^{2+}$ can be used, preferred are $Li^+$, $Na^+$, $K^+$, $Cs^+$, $Mg^{2+}$, $Ca^{2+}$ and $Zn^{2+}$ and especially preferred are $Li^+$ and $Na^+$.

Especially preferred are the lysine salts of (2R,4R)-2-methylthiazolidine-2,4-dicarboxylic acid, (2S,4R)-2-methylthiazolidine-2,4-dicarboxylic acid and/or (2RS,4R)-2-methylthiazolidine-2,4-dicarboxylic acid.

The term (2RS,4R)-2-methylthiazolidine-2,4-dicarboxylic acid (2-MTDC) represents a diastereomeric mixture of the (2S,4R)-2-methylthiazolidine-2,4-dicarboxylic acid and the (2R,4R)-2-methylthiazolidine-2,4-dicarboxylic acid.

From DE-A-21 16 629 the synthesis of not diastereomerically pure 2-methylthiazolidine-2,4-dicarboxylic acid (2-MTDC), its use as a hepatoprotective agent as well as the preparation of not diastereomerically 2-methylthiazolidine-2,4-dicarboxylic acid, which is contained in pharmaceutical products in form of coated tablets or ointments is known. Not diastereomerically pure 2-MTDC was proposed for some applications as a pharmaceutical. The European patent application No. 989 16 811 sets forth the use of not diastereomerically pure 2-MTDC as a mucolytic agent and the European patent application No. 989 16 809 describes a combination preparation from not diastereomerically pure 2-MTDC and paracetamol. The use of salts of 2-MTDC is preferred for prophylaxis and/or treatment of neurodegenerative diseases, especially the salts with amino acids, whereas the lysine salts are preferred. Preferred as well is the use of diastereomerically pure (2R,4R)-2-methylthiazolidine-2,4-dicarboxylic acid or (2S,4R)-2-methylthiazolidine-2,4-dicarboxylic acid in form of their salts, especially the salts with amino acids.

Thus, according to invention the salts of 2-MTDC, (2R, 4R)-2-methylthiazolidine-2,4-dicarboxylic acid and/or (2S, 4R)-2-methylthiazolidine-2,4-dicarboxylic acid can be used for preparation of a pharmaceutic formulation for prophylaxis and/or treatment of neurodegenerative diseases, especially of Parkinson's disease, Huntington's chorea, cerebral circulatory disorders, ischemia, cerebral ischemia, apoplexy, cerebral apoplexy, brain deficiencies, senile dementia or Alzheimer's disease. Besides the salts also the salt free compounds (2R,4R)-2-methylthiazolidine-2,4-dicarboxylic acid, (2S,4R)-2-methylthiazolidine-2,4-dicarboxylic acid as well as (2RS,4R)-2-methylthiazolidine-2,4-dicarboxylic acid are suitable for this application.

Experiments were carried out for evidence of the activity of the free compounds as well as of the salts of 2-MTDC, (2R,4R)-2-methylthiazolidine-2,4-dicarboxylic acid and/or (2S,4R)-2-methylthiazolidine-2,4-dicarboxylic acid, which should determine the effects of lysine salts onto the concentrations of dopamine in the substantia nigra and the striatum, its metabolites 3,4-dihyroxyphenylacetic acid (DOPAC) and homovanillinic acid (HVA) and onto 5-hydroxytryptamine (5-HT, serotonine) and its metabolite 5-hydroxyindoleacetic acid (5-HIAA).

Furthermore, the concentration of 3-methoxytrytamine was measured, an indicator substance for the in vivo activity of dopaminergic neurons. It is generated extraneuronally from dopamine via methylation of the hydroxyl group in position 3 by the catechol-O-methyltransferase (COMT). This means, that only dopamine, which was released during the activity of the dopaminergic nerve cells, can be the substrate of the enzyme. The more active these are the higher is the concentration of 3-methoxytyramine. The lysine salt of 2-MTDC was injected intraperitoneally four to five days before the measuring of 3-methoxytyramine.

It could be proven, that the lysine salt of 2-MTDC leads to an intense activation of the dopaminergic neurons. The inactivating effect of malonate is overcompensated by this effect. Thus, this observation is exciting, because the effect of the lysine salt of 2-MTDC is long persistent.

To investigate dopaminergic neurons which sensitively react as is known to neurotoxins what can lead e.g. to the Parkinson's disease the left and the right striatum were selected as brain regions. The dopaminergic cell bodies are localized in the substantia nigra and project their axons into the dorsal striatum. The beneath described execution of the experiments allows to investigate separately degenerative processes in the region of the cell appendages which normally degenerate first and in the cell bodies of the dopaminergic neurons which are more resistant compared to noxa.

As neurotoxic substance sodium malonate was chosen, because this mitochondrial toxin leads to an acute release of dopamine in the striatum of rats. Seven days after injecting the malonate it was proven that the concentration of dopamine decreased to 6% in the striatum compared to the contralateral striatum of the same animal. The effect of malonate on the dopamine concentration depends on time and dose rate.

Malonate is a competitive inhibitor of the succinate dehydrogenase (SDH). This mitochondrial enzyme plays a decisive role in the neuronal energy supply. It is involved in the tricarbonic acid cycle and in the oxidative phosphorylation. An intrastriatal injection of malonate initiates a lesion which appears excitotoxic and can be prevented via application of competitive and non competitive antagonists at the NMDA receptor. An intrastriatal injection of higher dose rates of malonate leads to lesions of dopaminergic and glutamatergic cell ends and to a considerable decrease of the striatal ATP concentrations and the concentration of dopamine. The excitotoxic processes activated by malonate which can lead to cell death are coupled to a bioenergetic deficiency. Both processes are supposed to participate in the pathogenesis of numerous neurodegenerative diseases such as Alzheimer's disease, Huntington's chorea and Parkinson's disease.

According to the invention, the salt free compounds and the salts of 2-MTDC, (2R,4R)-2-methylthiazolidine-2,4-dicarboxylic acid and/or (2S,4R)-2-methylthiazolidine-2,4-dicarboxylic acid can be used directly as salt free compound and salts respectively or manufactured as pharmaceutic formulation for prophylaxis and/or treatment of neurodegenerative diseases especially of Parkinson's disease, Huntington's chorea, cerebral circulatory disorders, ischemia, cerebral ischemia, apoplexy, cerebral apoplexy, brain deficiencies, senile dementia or Alzheimer's disease by administering a therapeutically effective amount of the corresponding salt free compound and the corresponding salt respectively to an individual suitable for prophylaxis and/or treatment of the particular neurodegenerative disease.

The term ischemia refers to the decrease or the interruption of the blood circulation of an organ, organ part or tissue due to insufficient arterial blood supply (e.g. by thrombosis, embolism, endarteriitis obliterans, vascular spasm or tumors). Thus cerebral ischemia signifies the decrease or the interruption of the brain's blood circulation. The consequences of ischemia can be hypoxia, infarction as well as necrosis.

Another object of the present invention are pharmaceutical formulations comprising the compounds (2R,4R)-2-methylthiazolidine-2,4-dicarboxylic acid, (2S,4R)-2-methylthiazolidine-2,4-dicarboxylic acid, (2RS,4R)-2-methylthiazolidine-2,4-dicarboxylic acid and/or salts of these compounds as pharmaceutically active agent optionally together with physiologically compatible carriers, auxiliary materials, fillers, flavor or color additives and/or solvents as well as diluents.

The compounds applicable according to invention as well as the pharmaceutic formulations applicable according to invention are suitable for an intravenous, intraperitoneal, intramuscular, subcutaneous, rectal, transdermal, oral, nasal, buccal, sublingual or any other application. Especially preferred is the oral and parenteral administration of the compounds according to the invention.

The compounds according to the invention are applied in a dose rate from 1 to 10,000 mg, preferred 10 to 5,000 mg and especially preferred from 50 to 1,000 mg.

The pharmaceuticals according to the invention are prepared with conventional solid or liquid carriers or diluents and the conventionally utilized pharmaceutical auxiliary materials corresponding to the desired type of application with a suitable dosage in a known manner. Such pharmaceutical forms are e.g. tablets, film-coated tablets, coated tablets, capsules, pills, powders, solutions, dispersions, suspensions, depot forms or inhalation solutions.

Also parenteral formulations such as injection or infusion solutions come of course into consideration. Further on, formulations such as suppositories shall be mentioned.

Corresponding tablets can be obtained, for instance, by mixing the compounds according to invention with known auxiliary materials for example inert diluents such as dextrose, sugar, sorbitol, mannite, polyvinylpyrrolidone, blasting agents such as corn starch or alginic acid, adhesive agents such as starch or gelatine, lubricants such as magnesium stearate or talc and/or agents for achieving a repository effect such as carboxypolymethylene, carboxymethyl cellulose, cellulose acetatephthalate or polyvinylacetate. The tablets can be composed of several layers.

Accordingly coated tablets can be prepared by coating of cores which were manufactured analogous to the tablets with agents typically used in coated tablet coatings such as polyvinylpyrrolidone or shellac, rubber arabicum, talc, titan dioxide or sugar. Thereby also the coated tablet cover can be composed of several layers whereas the auxiliary materials mentioned in case of the tablets above can be utilized.

In addition, solutions or suspensions comprising the active agent which can be used according to the invention can contain flavor ameliorative agents such as saccharine, cyclamate or sugar as well as flavoring substances such as vanillin or orange essence. Furthermore, they can contain suspension auxiliary materials such as sodium carboxymethyl cellulose or preservatives such as p-hydroxybenzoate. Capsules which contain active agents can be prepared, for example, by mixing the active agent with an inert substrate such as lactose or sorbitol and encapsulating them into gelatine capsules.

Suitable suppositories can be prepared, for example, by mixing with substrates provided therefor such as neutral greases or polyethylene glycol and derivatives thereof respectively.

Methods for preparing several formulations as well as the different application techniques are known to the person skilled in the art and described in detail, for instance, in "Remington's Pharmaceutical Sciences, Mack publishing Co., Easton Pa.".

EXAMPLES

The term 2-MTDC refers to (2R,4R)-2-methylthiazolidine-2,4-dicarboxylic acid, (2S,4R)-2-methylthiazolidine-2,4-dicarboxylic acid as well as (2RS,4R)-2-methylthiazolidine-2,4-dicarboxylic acid, whereas 2-MTDC however preferably refers to the racemic compound.

Example 1

Preparation of the Lysine Salt of 2-MTDC

1. Prearrangement of a 4 N Potassium Acetate Solution:

294.45 g (3 mol) potassium acetate (pure, DAB) are resolved in approx. 400 ml of demineralized water whereas the solution warms and is adjusted to an end volume of 750 ml after cooling down to 25° C. (±5° C.) in a 1 l measuring cylinder.

2. Reaction:

In a 4 l round-bottomed flask 394.03 g (2.5 mol) cys*HCl in 545 ml MeOH are suspended under stirring and 1.2 l of isopropyl alcohol is added. First about 125 ml 4 N potassium acetate solution is added. Considerable amounts of a white precipitate are formed. To this suspension 243 ml (±2.5 ml) pyruvic acid are added. The utilized measuring cylinder is rinsed with 75 ml of isopropyl alcohol in total. Immediately after addition of the pyruvic acid the residual amount of 4 N potassium acetate solution is added, the well stirable suspension warms up to approx. 40° C. and during 4 h the temperature decreases slowly to RT. The stirring is stopped and the reaction mixture is kept at 4° C. for 16 hours (i.e.

over night). In doing so the precipitate deposits and a lightly yellow supernatant is received.

3. Purification

The precipitate is filtered under suction via a Büchner funnel, pressed to dryness and is taken up two times in approx. 150 ml of demineralized water, filtered under suction and pressed to dryness. High vacuum oven desiccation follows at approx. 40° C.

The raw product is added to approx. 900 ml of boiling demineralized water under intensive stirring (no magnetic stirrer!). It is heated carefully for approx. 10 minutes, whereas the viscous slurry is stirred intensively. Afterwards the suspension is cooled and filtered after standing for 3 hours under suction, pressed to dryness, taken up in approx. 150 ml of ice cold demineralized water, filtered under suction and again pressed to dryness. Afterwards high vacuum oven desiccation follows at approx. 40° C. until constant mass (cold trap change). The obtained product is crushed.

Yield: 354 g (74% of theory)

4. Lysine Salt 10 mmol of MTDC and 20 mmol of L-lysine base are dissolved in 20 ml of water at room temperature. The transparent solution is then lyophilized. In the solution no pyruvic acid or free cysteine could be detected.

Example 2

Animal Experiments:

In a test series 2×0.8 mmol/kg 2-MTDC lysine salt (2-MTDC-lys) was applied intraperitoneally to rats after 12 h and 48 h. 30 minutes after the last application the one half of the rats received 2 μmol of sodium malonate into the left striatum via an afore stereotactically implanted guide cannula. The right striatum was used as intraindividual control tissue. Four days after the last application the concentrations of the transmitters and of their metabolites were measured.

Another group of rats received solvents into the left striatum and a third group received 2 μmol of sodium malonate into the left striatum.

Description of the Experiments:

A group of 6 Wistar rats, Charles River, Sulzbach Rosenberg receive two times intraperitoneally applied 0.8 mmol/5 ml/kg body weight 2-MTDC-lys within 48 h. 30 minutes after the second application 2 μmol of sodium malonate (Sigma) dissolved in physiological common salt solution are applied stereotactically during general anesthesia (ketamine 80 mg/kg and xylazine 6–10 mg/kg (IM)) via a syringe with an attached precision pump directly into the left striatum (flow rate: 0.5 μl/min, total volume 2 μl).

Four days after the last application the striatum and the substantia nigra of the treated side as well as of the other side is excised separately in each case, balanced and the tissue is homogenized in 0.1 molar perchloric acid (a striatum in 500 μl, a substantia nigra in 150 μl) and is centrifuged afterwards at 13,000 rpm for 5 minutes (Biofuge 13, Heraeus). The supernatant is filtrated at 10,000 rpm for 10 minutes (Millipore, 0.22 μm pore size). Aliquots of the eluent are injected directly into the HPLC apparatus. Dopamine, DOPAC, HVA, 5-HT, 5HIAA and 3-methoxytyramine are separated via HPLC-ELCD and quantified colorimetrically. As the concentration of dopamine relative to the concentration of the metabolites is high in the striatum dopamine is measured in the striatum separately (conditions: 2 μl injection volume, detector adjusted to 20 nAmp).

The conditions for the other substances and the substantia nigra are as follows: 5 μl injection volume, detector: 5 nAmp.

Another group of rats receives intraperitoneally solvents within 48 h (four times 50% propanediol as well as two times physiological common salt solution in each case 5 ml/kg) and 30 minutes after the last application 2 μmol sodium malonate is injected intrastriatally left. The second test procedure is equivalent to the above described.

A third group of rats receives intraperitoneally solvents within 48 h (four times 50% propanediol and two times physiological common salt solution in each case 5 ml/kg) and 30 minutes after the last application 2 μl physiological common salt solution is injected into the left striatum. The further test procedure is equivalent to the above described.

Results:

The lysine salt of 2-MTDC (2-MTDC-lys) solely has no influence on the concentration of dopamine, DOPAC, HVA. A pretreatment with 2-MTDC-lys however prevents the toxic effect of malonate. 2-MTDC-lys acts neuroprotectively as it prevents the effect of malonate on the reduction of the dopamine and dopamine metabolites concentrations respectively.

In the chosen dose rate and during the examination period of four days calculated from the last application 2-MTDC-lys affects obviously dopaminergic neurons but not serotonergic neurons. The effects onto dopaminergic neurons comprise a long persistent activation which is probably also the reason for the neuroprotection. The treatment with 2-MTDC-lys prevents the neurodegeneration as well of the nerve ends in the striatum as of the cell bodies in the substantia nigra (prophylactically neuroprotective).

The test series of example 2 was repeated whereas the lysine salt of 2-MTDC was replaced by the sodium salt. It could be shown that also the sodium salt of 2-MTDC provides comparable results.

Example 3

Therapeutic Effect of 2-MTDC and Salts Thereof

In another animal experiment model (apoplexy model) it could be shown (examples 3 and 4) that 2-MTDC as well as salts of 2-MTDC have a cerebroprotective effect. As well the free acids of 2-MTDC [(2R,4R)-2-methylthiazolidine-2,4-dicarboxylic acid, (2S,4R)-2-methylthiazolidine-2,4-dicarboxylic acid, (2RS,4R)-2-methylthiazolidine-2,4-dicarboxylic acid] as, for instance, the lysine salts of 2-MTDC are capable of reducing the infarction extent induced by occlusion of the cerebral artery in mice (MNRI mice). These results are described in the following on the example of the sodium salt of 2-MTDC.

Sodium Salts of 2-MTDC (2-MTDC-Na)

The following test series deals with the examination of the neuroprotective effect of 2-MTDC-Na in application of 2-MTDC-Na after the ischemia.

Description of the Experiments

Per test group 13 through 16 MNRI mice were employed. The middle cerebral artery of the mice was occluded according to the method of Welsh (F. A. Welsh, T. Sakamoto, A. E. McKee, R. E. Sims, J. Neurochem. 1987, 49, 846–851). For that purpose the mice are anesthetized with tribromoethanol (600 mg/kg body weight, intraperitoneally). Immediately after the anesthesia a small cavity was drilled into the mice cranium to lay open the middle cerebral artery. The strain as well as both arms of the middle cerebral artery were occluded via electro coagulation. Meanwhile the blood heat of the mice was kept on 37° C.±1° C. by utilizing a heating lamp. Subsequently the mice were kept at a surrounding temperature of 30° C. for another 2 h.

One group of mice was injected intraperitoneally 2-MTDC-Na (200 mg/kg 2-MTDC-Na dissolved in 0.9% NaCl solution) 15 minutes after and another group 60 minutes after the occlusion of the middle cerebral artery. A third group received the vehicle only (0.9% NaCl solution without 2-MTDC-Na).

For the following histologic examination 2 days after the occlusion of the middle cerebral artery the mice were anesthetized again with tribromoethanol and received intraperitoneally applied 0.5 ml of a 1.5% solution of neutral red (toluylene red, Acros Chimica) in addition. The brains were extracted and kept for 24 h in a fixative solution (4% formalin with phosphate buffer at pH 7.4).

The tissue on the surface of the brain which was not colored by neutral red was measured as surface region affected by infarction under utilizing a color analysis system (Kontron, Eching, Germany) (C. Backhauβ, C. Karkoutly, M. Welsh, J. Krieglstein, J. Pharmacol Toxicol Methods, 1992, 27 (2), 27–32).

Results

Infarction formation could only be proved at the cortical tissue. Moreover, the infarction volume correlated with the infarction surface. 2-MTDC-Na was capable of reducing significantly the area of the brain which was affected by the infarction whereas it seems to be important to apply 2-MTDC-Na after the occlusion of the middle cerebral artery as soon as possible. In the test series where 2-MTDC-Na was injected one hour after the occlusion of the middle cerebral artery only a strongly attenuated effect of the infarction reduction was shown.

Thus, it could be shown that 2-MTDC-Na administered after the ischemia exhibits further on its neuroprotective effect whereas the therapeutical window for the application of 2-MTDC-Na is about 60 minutes after the occlusion of the middle cerebral artery.

Example 4

Protective Effect of 2-MTDC and Salts Thereof

The execution of the test according to example 3 was repeated whereas 2-MTDC-Na was applied one hour before the occlusion of the middle cerebral artery (MCA-O: occlusion of the middle cerebral artery).

It could be shown that 2-MTDC-Na protects the brain of the animals against damages which were caused by cerebral ischemia, if 1 h before the occlusion of the middle cerebral artery the 2-MTDC-Na is injected intraperitoneally at a concentration of 200 mg/kg body weight of the test animal.

The test series according to example 3 and 4 were repeated with 2-MTDC-lys as well as with the free acid of 2-MTDC instead of 2-MTDC-Na. The experiments with 2-MTDC-lys and the free acid of 2-MTDC produced similar results as the experiments with 2-MTDC-Na.

What is claimed is:

1. A method of treating neurodegenerative diseases selected from the group consisting of Parkinson, Huntington's chorea, cerebral circulatory disorders, ischemia, cerebral ischemia, apoplexy, cerebral apoplexy, senile dementia, and Alzheimer's disease, comprising administering (2R, 4R)-2-methylthiazolidine-2,4-dicarboxylic acid, (2S,4R)-2-methylthiazolidine-2,4-dicarboxylic acid and/or (2RS,4R)-2-methylthiazolidine-2,4-dicarboxylic acid as well as their salts to a patient in need thereof.

2. The method, according to claim 1 wherein (2R,4R)-2-methylthiazolidine-2,4-dicarboxylic acid, (2S,4R)-2-methylthiazolidine-2,4-dicarboxylic acid, and/or (2RS,4R)-2-methylthiazolidine-2,4-dicarboxylic acid is administered in a dose rate of 1–10,000 mg, especially from 10–5,000mg.

* * * * *